(12) United States Patent
Herman

(10) Patent No.: US 9,018,402 B2
(45) Date of Patent: Apr. 28, 2015

(54) PRODUCTION AND USE OF 1,2,4-TRIOXOLANE COMPOUNDS, OZONIDES, WITH BLEACHING PROPERTIES FOR THE WHITENING OF TEETH, SKIN, AND HAIR

(71) Applicant: Ross Michael Herman, Riverside, CA (US)

(72) Inventor: Ross Michael Herman, Riverside, CA (US)

(73) Assignee: Ross M. Herman, Riverside, CA (US)

( * ) Notice: Subject to any disclaimer, the term of this patent is extended or adjusted under 35 U.S.C. 154(b) by 0 days.

(21) Appl. No.: 13/792,071

(22) Filed: Mar. 10, 2013

(65) Prior Publication Data

US 2014/0256962 A1 Sep. 11, 2014

(51) Int. Cl.
*A61K 8/49* (2006.01)
*A61Q 19/02* (2006.01)
*A61Q 5/08* (2006.01)
*A61Q 11/00* (2006.01)

(52) U.S. Cl.
CPC ............. *A61K 8/4973* (2013.01); *A61Q 19/02* (2013.01); *A61Q 5/08* (2013.01); *A61Q 11/00* (2013.01)

(58) Field of Classification Search
USPC ............................................. 549/431; 424/62
See application file for complete search history.

(56) References Cited

FOREIGN PATENT DOCUMENTS

| CN | 101508634 B | * | 9/2011 | .............. C07C 47/21 |
| CN | 102351697 A | * | 2/2012 | .............. C07C 69/67 |

OTHER PUBLICATIONS

Goodwin et al., Crystalline Ozonides from cis-trans-Ethylene Derivatives, 1953, Journal of the American Chemical Society, 75, 4273-4275.*
Pryor et al., Ozonation of Methyl Oleate in Hexane, in a Thin Film, in SDS Micelles, and in Distearoylphosphatidylcholine Liposomes: Yields and Properties of the Criegee Ozonide, 1992, Chem. Res. Toxicol., 5, 505-511.*

* cited by examiner

*Primary Examiner* — Kristin Vajda

(57) ABSTRACT

Stable, bio-compatible, 1,2,4-Trioxolane compounds are produced and applied to living tissue, teeth, and hair, for the cosmetic purpose of bleaching or whitening.

1 Claim, 3 Drawing Sheets

PRODUCTION AND USE OF 1,2,4-TRIOXOLANE COMPOUNDS, OZONIDES, WITH BLEACHING PROPERTIES FOR THE WHITENING OF TEETH, SKIN, AND HAIR

RELATED APPLICATIONS

Not applicable

FEDERALLY SPONSORED RESEARCH

Not applicable

SEQUENCE LISTING

Not applicable

BACKGROUND

First, previous uses and claims of ozonide compounds, class 549, sub class 431. And second, prior art of; teeth/tooth, hair, and skin, whitening or bleaching, class 424, sub classes 62, and 53, and class 433, sub class 216.

PRIOR ART

Related to Ozonides

Ozonides are produced by the ozonation[1] of alkenes, as depicted in FIG. 1. The production of a 1,2,4-trioxolane compound is highly dependent on both the structure of the alkene being ozonated, and on the conditions of the reaction. Many alkenes will not produce 1,2,4-trioxolanes, as the major product, regardless of reaction conditions.

Ozonolysis was invented by Christian Friedrich Schonbein ca.1840 as a method of structural determination for organic molecules with double bonds.

Between 1903 and 1948 Carl Harries studied the physical and chemical properties of ozonides.

In 1949 Rudolf Criegee, now considered the father of modern ozone chemistry, started more thorough experimentation with ozone chemistry, and with the help of his protege Philip Bailey elucidated much of the mechanisms of ozonolysis. Philip Bailey published a comprehensive review[2] of ozone chemistry in 1978, which still stands as the preeminent reference for the reactions with ozone. It was not until 1953 however, that Rudolf Criegee rigorously established the mechanism of ozonolysis and the structure of ozonides.

Since that time, the term ozonide has some degree of ambiguity, as the term ozonide can refer to either the 1,2,4-trioxolane structure, or it can refer to an extremely complicated mixture of compounds that are produced by the ozonation of natural oils, waxes, or rubbers. These complicated mixtures are typically hydro-peroxides and their polymers, along with some ozonides and diperoxides. Typically the older literature uses the term ozonide as any product of ozonation, however some contemporary literature may do the same.

For this discussion the term ozonide will refer to 1,2,4-trioxolane compounds, sometimes referred to as the secondary ozonides in chemical literature. Thus an ozonide, or 1,2,4-trioxolane, is distinguished from the complicated mixture of compounds produced by the reaction of ozone with unsaturated mixtures like oils, waxes, and rubbers.

Inventors have been claiming dramatic medicinal uses for ozonides since 1902 when William Neel[3] first described the medicinal use of ozonides for diseases of the blood and respiratory organs, where ozonated oils were inhaled.

Then in 1917 William J. Knox[4] ozonated ricinoleic acid or caster oil to produce a germicidal laxative.

In 1921 James Todd published "Experiments with Oxygen on Disease" (Pittsburgh, Pa.) where he detailed the manufacture of ozonated olive, and cod-liver oils, that give "miraculous cures" with oral dosages.

In 1942 Charles C. Johnsons described the ozonation of the purified triglyceride of oleic acid, and its fungicidal, germicidal, and deodorizing applications.

Georg Cronheim[6] published a thorough review of the pharmaceutical uses of ozonides in the Journal of the American Pharmaceutical Association (now known as, Journal of Pharmaceutical Sciences) that covered all known uses of ozonides up to 1947. All the uses of ozonides described by Cronheim were of topical preparations with germicidal properties, with one significant exception, where Butz and La Lande[7] studied the anthelmintic action of several ozonized oleic acid esters, in dogs infested with ascarides. This is the first example in the literature where the ozonide of methyl oleate (the same compound described in this patent application) was prepared, and used for a purpose.

In 1986 De Villez[8] used ozonated oils to treatment acne.

From 1988 to 1994 Stephen Herman[9] generated a long list of patent publications, and a far longer list of claims for the uses of ozonides. The list of claims covers thousands compounds, and hundreds of uses. I will list several of the uses described: treatment for insect stings, athletes foot, nail fungus, warts, viral infection, HIV, insecticide, fungicide, sunburn, serious burn repair, scar inhibitor, cancer, spermicide, arthritis, protozoal infection, leishmaniasis, and many dozens of other medical applications.

In 1994 Davy K. Koech[10] reports "Trioxolanes: a new generation of compounds with Wide Ranging Activities". And in 2008 Koech et al.[11] published "Clinical Applications of Trioxolane Derivatives" where he specifically indicates, Methyl-5-octyl-1,2,4-trioxolane-3-(8-octanoate), as a compound prepared and used for a purpose, in this case the treatment of both AIDS and arthritis. This is the second example from literature where the ozonide of methyl oleate is prepared and used for a purpose.

In 1999 Dr. Gerhard Steidl published "The Fight Against Bacteria, Funguses, and Parasites by Supporting the Oxidative System in the Human Organism". This is the first of three papers published by Dr. Steidl concerning the use of ozonides. The second and third papers are titled, "Medicinal Microbiology Elimination of Pathogenic Bacteria, Fungi, Parasites, Viruses by Oxygen and Bitter Drugs" (September 2000), and the more extensive follow-on paper, "Use of Ozonides in the Treatment of Malignant Disease—basic principles and clinical results" (January 2002). These documents seem to be web based publications found by a web search of the titles. Dr. Gerhard Steidls' papers again describe hundreds of medical applications where virtually all known parasitic, viral, fungal, and tumor cells, can be treated, at least partially, as bitter drugs are used concomitantly with an ozonized oil. I would like to add that Dr. Steidl also suggests that some forms of depression, anxiety, hyperactivity, and hypo-activity may also be treated with these oxidative therapies.

Sasaki et al[12] claim anti tumor activity with an ozonide.

In September 2004 Hofmann et al[13] describe the treatment of coronary arteriosclerosis by an oxidative therapeutic formulation, followed in April 2005 by a second patent[14] describing the successful treatment of horses infected with sarcocystis protozoal infections. And a third patent[15] issued in 2009 describes the bone regeneration properties of these oxidative therapies.

The most recent excitement surrounding the use of ozonides is related to the treatment of malaria. I feel this is largely due to recent comment by WHO, where they open the door for the use of these types of compounds for malarial infestations. Many researches seem surprised by the effectiveness of artemisinin (a naturally occurring compound with very similar structure to a trioxolane), and other synthetic trioxolane compounds[16] [17] for the treatment malaria. Most notable is the patent by Vennerstrom et al.[18] claiming anitmalarial activity with their ozonide, even thought it is obvious to me that any compound with a trioxolane functionality would have some degree of effectiveness for all types parasitic infestations.

PRIOR ART

Related to Tooth, Skin, and Hair Whitening

Many thousands of patents have been issued relating to the whitening of, teeth, skin and hair. With only a few exceptions that I will mention next, every chemical formulation described for said whitening purposes incorporates some form of hydrogen peroxide, as a hydrogen peroxide salt or as hydrogen peroxide complex, as the actual bleaching agent. The most recent patents add elements to the existing hydrogen peroxide technology to improve bleaching. These improvements are related to the activation of hydrogen peroxide compounds by heat, laser light, and most recently metal ions or oxides as a catalytic source of activation.

Speronello et al.[19] purpose the use of chlorine dioxide as an alternative the hydrogen peroxide for bleaching teeth.

Edward Lynch[20] proposed the use of ozone gas as a tooth whitener.

And the most closely related prior art might be, US patent 2009/0285767 A1, where James Shenberg describes using ozone dissolved in a liquid as a means to whiten teeth. Interestingly Shenberg suggests the use of a peroxide based tooth whitening composition in addition to the dissolved ozone.

SUMMARY

Stable ozonides are produced that are bio-compatible with living tissue. These ozonides can be applied, in appropriate concentrations, to the skin, teeth, or hair, for the purpose of whitening, or bleaching.

Additionally I would like to mention that the ramifications of this invention are extensive, as ozonides could be used to effectively treat thousands of disease conditions, from arthritis and AIDS to nail fungus, malaria, and warts. Unfortunately however I do not believe that these types of therapies will be allowed into the market place, as it could mean billions of dollars in lost revenue for the FDA and its associated pharmaceutical industry. I do however see many cosmetic applications as a viable alternative for the uses of ozonides.

DESCRIPTION OF FIGURES

Drawings

DETAILED DESCRIPTION OF INVENTION

Figure 1:
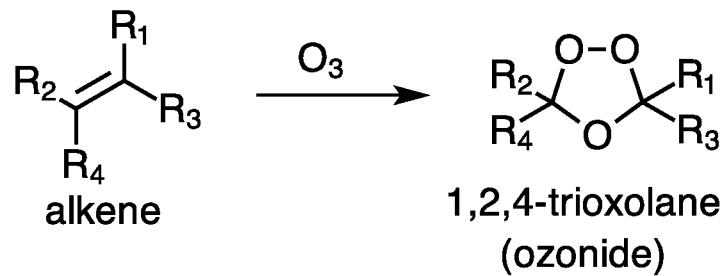
FIG. 1 depicts the chemical reaction of ozone with any alkene. Where the R-groups can be any alkyl group or proton.

Any compound with a 1,2,4-trioxolane functionality will have some degree of bleaching power, thus a virtually infinite variety of compounds could be created with some degree of bleaching properties. FIG. 1. depicts the formation of these embodiments, where the alkene substituents can be any alkyl group or proton. Resulting in an ozonide of infinite variety.

Figure 2:
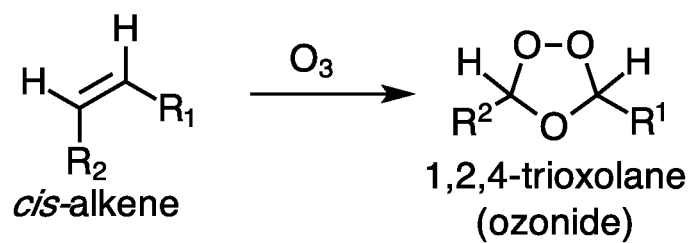
FIG. 2 depicts the practical embodiments of ozonide production. R1 represents a hydrocarbon moiety with between 2 and 30 carbon atoms and may containing other cis-alkene functionalities. And R2 represents an organic moiety with between 2 and 30 carbon atoms and also may contain an ester, or derivative of an ester. Additionally, the methyl ester of oleic acid is excluded from this claim (in other words, for the case where R1 is a straight chain eight carbon moiety and R2 is an ester with seven carbon atoms connecting the carbonyl atom with the unsaturated carbon, then the ester moiety must be other than a methyl group).

Fortunately however, due to the many practical concerns regarding the synthetic process, the nature of the desired product, and the availability of unsaturated hydrocarbons (alkenes), the practical embodiments are more narrowly defined by FIG. 2. FIG. 2 thus depicts the practical ramifications of this invention. FIG. 2 shows that the alkene to be ozonated must have only two alkyl substituents, and these two substituents must be in a cis orientation. Now the exact nature of these two cis-alkyl substituents thus complete the definition of the practical embodiments of this invention. R1 is an alkyl group of chain length C2-C30, and may contain other cis-alkene functionalities. R2 is an alkyl group of chain length C2-C30 that may also contain an ester group or other functionality. The exact nature of these two R-groups is left undefined so as to allow for differing log P values (log P value, a physical characteristic a pharmaceutical compound used to predict its behavior within biological systems) and formulation characteristics. For example if aqueous formulations were desirable, then salts of the ozonide could be prepared. Also, a specific log P value of the product could be targeted by manipulation of these R-groups.

Figure 3:
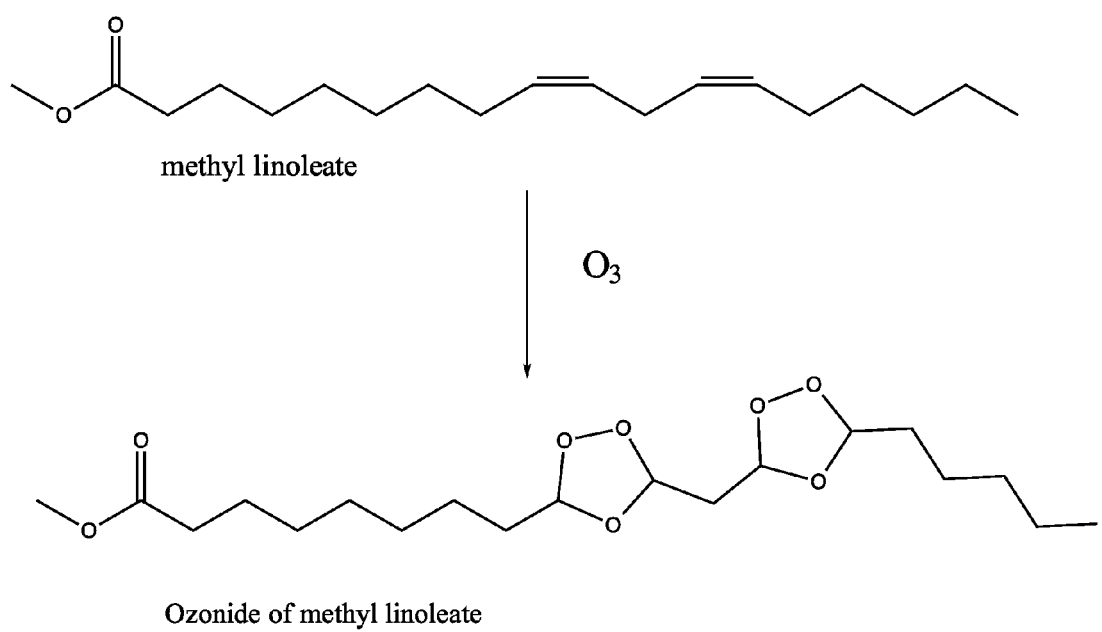
FIG. 3 is the chemical reaction that shows the formation of a specific embodiment of this invention, where the cis-Alkene, methyl linoleate (CAS#112-63-0) is converted to the di-trioxolane depicted.

A specific embodiment of this invention is depicted in FIG. 3 showing the chemical reaction where the cis-Alkene methyl linoleate (CAS#112-63-0) is converted to the methyl linoleate ozonide, a di-trioxolane, under the following reaction conditions:

A 0.3M solution of methyl linoleate in hexane is maintained at −30 C, before using a sintered glass gas impinger to pass an oxygen stream containing about 5% ozone through the alkene solution. The effluent gas is monitored for the point when the ozone escaping the reaction is no longer being "absorbed" by the alkene solution. The reaction is very rapid and virtually quantitative, with >80% yields always expected. The hexane can then be thoroughly removed under vacuum (recovered, re-distilled, and reused) giving a product of sufficient quality for formulation and use.

Sources of methyl linoleate (CAS#112-63-0) are available world wide as it is used for a very wide variety of applications from, metal cutting lubricants and ink solvents to food emulsifiers and emollients in skin products.

As these compounds are subject to decomposition by both heat and light and should be stored in dark bottles, refrigerated, for best shelf life.

Figure 4:
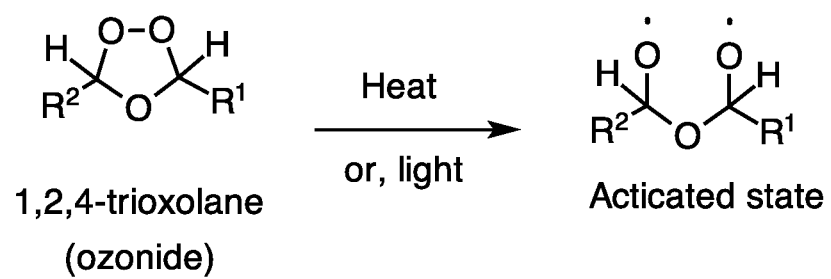
FIG. 4 depicts the chemical activation of on ozonide by heat or light, as taken from page 142 of Baileys review[21].

It is this same "decomposition" that can better be described as activation for the purposes of bleaching. As is the case with peroxide compounds, the bleaching rate for 1,2,4-trioxolane compounds can also be "activated" by either heat or by light, as depicted in FIG. 4 (taken from page 142 of Baileys review). And while the literature is vague for the specific wavelengths of light that activate the peroxide bond, wavelengths of between 375 and 500 nm have been used successfully for hydrogen peroxide and are expected to do the same with the peroxide bond in ozonides.

I have found no examples in the literature for an ozonide, or trioxolane compound being used for cosmetic purposes. However I still feel I should make some comments about how ozonides differ from hydrogen peroxide as a bleaching agent, since hydrogen peroxide currently constitutes the overwhelming majority of treatments for the bleaching of teeth, skin and hair.

Trioxolane compounds can be considered to have a negative toxicity, as not only are they highly tolerated by biological tissue but they can also purge the tissue of unwanted pathogens, like fungus, viruses, bacteria, and parasites. Hydrogen peroxide, on the other hand, is known to produce hydroxide radicals as the primary decomposition product. These hydroxide radicals are clearly the souse of tissue irritation produced by hydrogen peroxide treatments. This makes ozonides a much safer source of "peroxide like" whitening activity.

One disadvantage of the specific embodiment disclosed in this document is that on weight per weight basis hydrogen peroxide will have significantly more bleaching power, as the molecular weight of hydrogen peroxide is 11.4 times less than that of the ozonide disclosed herein. Hydrogen peroxide has a molecular weight of 34, compared with a molecular weight of 390 amu for the particular embodiment described here. Thus, If we assume the peroxide bond in the ozonide is of equal bleaching power to the peroxide bond in hydrogen peroxide, and with two peroxide bonds per molecule, then the ozonide will inherently have 6 times weaker, or milder, bleaching power.

[1] Criegee, Rudolf (1975). "Mechanism of Ozonolysis". *Angew. Chem. Int. Ed. Engl.* 14(11): 745-752.
[2] Bailey, P. S., "Ozonation in organic chemistry", Volume 1 olefinic compounds. Academic Press, New York (1978).
[3] Neel, W. D., U.S. Pat. No. 925,590 (July 1902)
[4] Knox, W. J., U.S. Pat. No. 1,210,949 (January 1917)
[5] Johnson, C. C., U.S. Pat. No. 2,356,062 (August 1944)
[6] Cronheim, G., Organic Ozonides as Chemotherapeutic Agents, I & II, *J. of the American pharmaceutical association*, Vol. 36, issue 9, September 1947, pp 274-281
[7] Butz, L. W., and La Lande, W. A., *J. of the American Pharmaceutical Association*, Vol 26, issue 2, pp. 114-121 (1937).
[8] De Villez, U.S. Pat. No. 4,451,480 and U.S. Pat. No. 4,591,602
[9] Herman, Stephen. EP0427781 A4, EP0476054 A4, U.S. Pat. No. 4,983,637, U.S. Pat. No. 5,086,076, U.S. Pat. No. 5,093,326, U.S. Pat. No. 5,126,376, U.S. Pat. No. 5,190,977, U.S. Pat. No. 5,190,979, U.S. Pat. No. 5,260,342, U.S. Pat. No. 5,270,344, and U.S. Pat. No. 5,364,879.
[10] Koech et. al. "Trioxolanes: A New Generation of Compounds with Wide Ranging Activities", *Afr. J Health Sci.* Vol. 1 No. 4 (November 1994)
[11] Koech, D. K., "Clinical applications of trioxolane derivatives", *Afr. J Health Sci.*, Vol 15, No. 1-2, pp 1-5, 2008.
[12] U.S. Pat. No. 6,365,610 B1, April 2002
[13] Hofmann et al. U.S. Pat. No. 6,790,463 B2 (September 2004)
[14] Hofmann et al. U.S. Pat. No. 6,790,463 B2 (April 2005)
[15] Hofmann et al. U.S. Pat. No. 7,572,782 B2 (August 2009)
[16] Valecha, N., et al. *Clin Infect Dis*. Vol. 51, issue 6, pp 684-691, September 2010.
[17] Uhlemann et al. *Anitmicrobial Agents and Chemotherapy*, "Mechanisms of Antimalarial Action of the Synthetic Trioxolane RBX11160" Vol. 51, issue 2, pp 667-672 (February 2007).
[18] Vennerstrom et al. U.S. Pat. No. 8,067,620 B2 (November 2011).
[19] Speronello et al. U.S. Pat. No. 8,303,939 B2 (November 2012)
[20] Lynch, U.S. Pat. No. 6,877,985 B2 (April 2005)
[21] Bailey, P. S., "Ozonation in organic chemistry", Volume 1 olefinic compounds. Academic Press, New York (1978).

The invention claimed is:

1. 1,2,4-trioxolane compounds produced by ozonation of cis-alkenes which can be used for bleaching or whitening of living tissue, teeth, and hair and the specific structures of these 1,2,4-trioxolane compounds are depicted in FIG. 2, where R1 is an alkyl group of chain length C2-C30 that may contain other cis-alkene functionalities, and R2 is an alkyl group of chain length C2-C30 that may contain an ester group or other functionality; additionally, the methyl ester of oleic acid is excluded (in other words, for the case where R1 is a straight chain eight carbon moiety and R2 is an ester with seven carbon atoms connecting the carbonyl atom with the unsaturated carbon, then the ester moiety must be other than a methyl group);

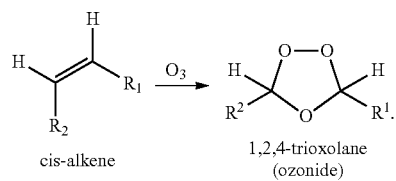

cis-alkene         1,2,4-trioxolane
                   (ozonide)

* * * * *